(12) United States Patent
Ehrlinspiel et al.

(10) Patent No.: US 8,216,293 B2
(45) Date of Patent: Jul. 10, 2012

(54) FLEXIBLE SHAFT

(76) Inventors: Michael Ehrlinspiel, Weingarten (DE);
Eric Flaxmeier, Karlsbad (DE)

( * ) Notice: Subject to any disclaimer, the term of this patent is extended or adjusted under 35 U.S.C. 154(b) by 1208 days.

(21) Appl. No.: 10/878,598

(22) Filed: Jun. 28, 2004

(65) Prior Publication Data
US 2008/0140216 A1     Jun. 12, 2008

(30) Foreign Application Priority Data
Jun. 26, 2003 (DE) .................. 103 28 882

(51) Int. Cl.
*A61F 2/06* (2006.01)
*A61F 2/74* (2006.01)
*A61F 11/00* (2006.01)
*A61M 29/00* (2006.01)

(52) U.S. Cl. ............... 623/1.11; 623/1.12; 623/1.15; 623/23.7; 606/108; 606/198

(58) Field of Classification Search ............ 606/153, 606/155, 198; 623/1.15, 1.16, 1.11, 1.12, 623/23.7
See application file for complete search history.

(56) References Cited

U.S. PATENT DOCUMENTS

| | | | | |
|---|---|---|---|---|
| 5,549,663 A * | 8/1996 | Cottone, Jr. | ............... | 623/1.22 |
| 5,746,691 A * | 5/1998 | Frantzen | ............... | 600/36 |
| 5,827,321 A * | 10/1998 | Roubin et al. | ............... | 623/1.16 |
| 6,395,020 B1 * | 5/2002 | Ley et al. | ............... | 623/1.15 |
| 6,537,202 B1 * | 3/2003 | Frantzen | ............... | 600/36 |
| 2002/0007209 A1 * | 1/2002 | Scheerder et al. | ............... | 623/1.15 |

OTHER PUBLICATIONS

Silva, Elson, Email Regarding Patent Application, Jun. 12, 2008.

\* cited by examiner

*Primary Examiner* — Gary Jackson
*Assistant Examiner* — Michael Mendoza
(74) *Attorney, Agent, or Firm* — McDonald Hopkins LLC

(57) ABSTRACT

A flexible shaft (28) to be inserted into a channel of a living body provided with a plurality of adjacently abutting cells (26), the walls (30) of which are formed from wall sections. For this reason the flexible shaft (28), which is particularly cost-effective to produce and which demonstrates high flexibility paired with ample stability, is constructed such that in at least one cell (26) in the cross-section of the wall (30) a concave wall section (44, 46, 48) is circumferentially alternated with a corresponding neighboring convex wall section (50, 52, 54).

18 Claims, 5 Drawing Sheets

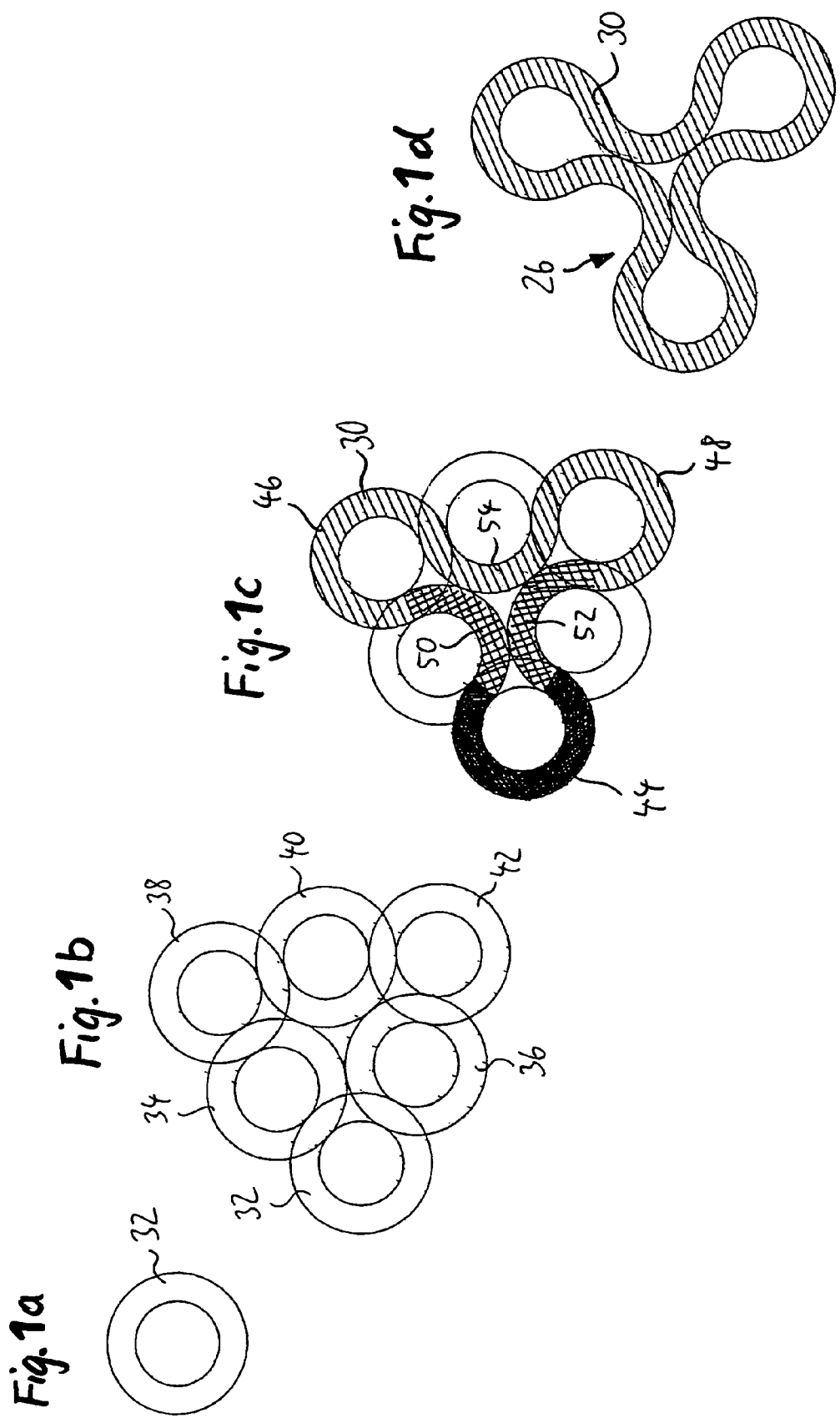

FLEXIBLE SHAFT

CROSS-REFERENCE TO RELATED APPLICATIONS

Figure 2C:
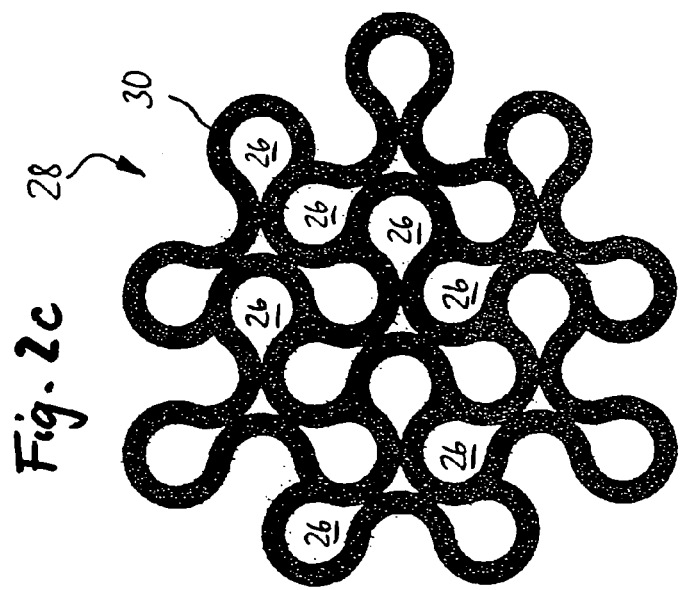

This application claims priority from German Patent Application No. 103 28 882.1-44 filed on Jun. 26, 2003.

DESCRIPTION

This invention relates to a flexible shaft to be inserted into a channel of a living body, having a plurality of abutting cells, the walls of which are composed of wall sections and the preferential use of same. The invention relates to, in particular, a flexible shaft that can be inserted into a lumen or a channel having varying characteristics. Such varying characteristics of the lumen can include curvatures, side branches, variable calibres or the varying resilience of the lumen walls.

Flexible shafts as described above could be used, for example, for stents inserted into different channels of a living body, such as, for example, the arteries, the esophagus, the scapha and the kidney channels. After insertion the stent must be radially expanded using a rod, e.g. a core, and this must be passed through the interior of the flexible shaft. To this end the flexible shaft must be hollow and must adapt to sinuous channel- and vein-like areas.

The aim of the invention is to produce a flexible shaft to be inserted into the lumen of a living body, which is cost-efficient to manufacture and which also possesses a high level of flexibility paired with ample stability, to be firmed up with a stent expansion rod, in particular. According to the invention this aim will be achieved using a flexible shaft as per Claim 1 and the use thereof as per Claim 8. The preferred embodiments are the subject matter of the claims below.

Accordingly, the aim, according to the invention with a first shaft, is achieved in that the wall of at least one cell, considered in cross-section, is constructed such that a concave wall section and a corresponding neighbouring convex wall section, alternate around the circumference thereof. The other advantageous embodiments of the invention are described in the claims below.

In the flexible shaft according to the terms of the invention, the wall is circumferentially constructed of adjacently abutting concave and convex wall sections. In this way, many sections are formed in the wall, in which, at the curves or deformations of the flexible shaft, each cell is stretched and unfolded to form firstly a folded concave and then a neighbouring convex wall section. The stretching of the folded concave and convex wall sections leads to the simultaneous enlargement of several cells in many areas of the wall.

The wall is simultaneously stretched and deployed in many areas at one time so that, during the bending and formation of the wall possessing several cells in many directional components, more than two directional components are formed, in particular. The shaft according to the invention will not, however, be radially compressed at the curve, such that the rod inserted into the curved shaft will not get stuck.

In the shaft according to the invention, the inner calibre at the bends or rather, the deformations, is slightly expanded where the stretched walls of the deformed cells, reinforced in the direction of a radial expansion of the shaft, press together.

According to the invention, the stretching procedure for the wall propagates itself further over the cell. The expansion of a cell in the wall of the flexible shaft according to the invention leads, in this way, to an equal formation over a large area of the wall structure. Undesirable locally-delimited and thus structure-debilitating formations are however, avoided in the invention.

On removal of the formation stress in a shaft according to the invention the almost percussive formation ceases without leaving any high residual stress in the shaft.

Furthermore, the wall of a shaft according to the invention is proportionally equally folded and undulated around the circumference thereof. Coating the wall with a lubricant, for example, facilitates shaping.

As a result of the equally undulated moulding of the wall, pressure peaks and formation peaks are avoided in the flexible shaft according to the invention. Moreover, narrow radii and the formation of varying radii is advantageously avoided, thereby avoiding, in particular, the danger of flaking or damage of the metal or ceramic wall coating of the shaft according to the invention. Moreover, the danger of a material capacity overload through pressure peaks is reduced. The material characteristics of the respective materials deployed are better exploited in the invention.

In a flexible shaft according to the invention the strength of the shaft materials increases under predefined conditions on cumulative formation. This so-called solidification effect can, according to the invention, be particularly well exploited, since the walls of the shaft are consistently and simultaneously formed to a comparatively small degree. The formation of the consolidation of the materials according to the invention can also be very accurately controlled and is, furthermore, pronounced across almost the entire shaft.

According to the invention, the wall of a cell of a shaft according to the invention alone is constructed from curved and folded, wall areas and junctions that butt up against such wall areas.

Moreover, the shaft according to the invention does not shorten itself axially on formation. A shaft according to the invention is characterised, rather, by the equal expansion of the cell structure in many directions.

The shaft according to the invention can again be particularly homogenously expanded and re-shrunk. This advantage can be used when the shaft needs to be prepared in an expanded or partly expanded condition. Furthermore, this advantage can be used in electropolishing and coating. The shaft can be stretched before treatment and be equally compressed again thereafter. The quality of the surfaces obtained through the process can therefore be improved.

The integration and shaping according to the invention of the varying deformation directions is, as already mentioned, specifically advantageous in the bend of the expanded shaft. The cells of a shaft according to the invention are deformed, expanding or shrinking according to their position in the line of the bend, thus enabling a homogenous bend in the shaft.

The invention can be particularly useful when the shaft is made from non-corrosive stainless steel, tantalum, niobium, cobalt alloys and other materials such as polymers and self-degradable materials (e.g. lactic acid material, lactic acid derivate, for example) and also when the shaft is made of Nitinol (a nickel-titanium alloy) and/or when other self-expansible materials such as materials with a shape memory are used.

In an advantageous development, the invention is constructed such that, when considered in cross-section, it has at least one wall section having a convex curve radius, which is substantially similar to the curve radius of a neighbouring concave wall section. Due to the substantial similarity of the curve radii of the folded walls of the cells, the shaft structure is particularly even. Such a shaft can, therefore, be electropolished or -plated particularly well. Again, coating procedures are facilitated, since the shading effect in so-called PVD or CVD procedures is avoided i.e. lessened and/or the bead effect of the exchange process (produced by the small radius capillary attraction) is avoided.

The above advantages of a flexible shaft according to the invention can be further declared advantageous, in that the wall sections are equal or almost equal when considered in cross-section. One such further developed shaft is constructed with exactly the same geometrical elements down to the junction. The geometrical elements can have identical inner and outer calibres and structural width. Such geometrical elements are formed through the heterogeneous nesting of a basic cell-shaped element.

Furthermore, when the wall sections are considered in cross-section it they visibly bear the advantage of being circular, arced and looped. Pressure peaks in the material of the shaft, can, in this way, be avoided and shaft torsion can be relieved.

It is further advantageous that at least one cell of at least three convex wall sections is moulded, when considered in cross-section, and in that there is a concave wall section between two convex wall sections. One in three such individual cells of a shaft according to the invention will not stretch in parallel to the others other during expansion. The directions used correspond substantially to an angle of 120°. For this reason, the flexible shaft according to the invention possesses a multi-axle deformation component having only two right-angled directional components which work in opposition to the above shaft, more easily expanding evenly as explained above.

The shaft according to the invention can be particularly highly compressed and light and evenly formed in that, when the compressed shaft is considered in cross-section, at least one cell of the convex wall sections adjacently abuts another.

According to the invention, we can, in addition to the above, describe as an advantage and defend the developments of the invention in the claims below for the invention also without the characteristics mentioned in Claim 1, whether as an individual item or in an independent interconnecting combination worthy of protection.

It is specified that the individual concave and convex wall sections according to the invention can be constructed using various types of moulding. These mouldings can be circular in cross-section or possess particularly short straight sections. The fundamental concept is that the wall of a cell of the flexible shaft is formed by alternately positioning concave and convex wall sections. The individual wall sections can be advantageously composed of one and the same basic geometrical element. These basic elements can be joined using joints, the outer conformation of which is particularly advantageous, again, having an external shape that is adapted to a basic element.

The flexible shaft so formed is also extremely advantageous as regards its achievable surface qualities and therewith its biocompatibility and required product engineering. In order to obtain a particularly good biocompatibility the shaft will be scrutinized, as any electrochemical polish, subject to surface finishing standards, which favour the production of a protective, straticulate surface film oxide. Such a process is based on a target compound removal from the surface of the shaft. The electro-polished surface has a very low coarseness and a very high purity. The polishing process is electrically assisted, passed through an acidic mixture, whereby, in order to obtain an even polish, as homogenous as possible a construction structure must be available. The shaft according to the invention is, as described above, made from this type of homogenous structure. Particularly large or small radii are avoided in the structure according to the invention. The known shafts, made from different construction components that merely concern the mechanical characteristics of the corresponding shaft will be optimized.

According to the invention, one application of a flexible shaft according to the invention or a preferred embodiment thereof is made available herewith for insertion or insertion and disposition of a spreading structure, a metal electrode and/or an endoprosthesis or stent in a hollow organ, lumen, channel or cavity.

In addition the flexible shaft can also, in a preferred embodiment, be used in a guide-wire body. Here the flexible shaft forms a highly flexible tip or a highly flexible distal extremity for the guide-wire. Consequently, optimal insertability into the target area is ensured, in that the flexible shaft structure, i.e. the flexible shaft, can be angled or bent continuously variably and without constraint, like a rubber hose. The flexible shaft can, in particular, possess high torsion rigidity, thus facilitating its insertion into small and constricted serpentine vessels. This is particularly advantageous when probing neurovascular blood vessels, such as, for example, the Aorta vertebralis, the Aorta cerebralis or the Aorta carotis.

The flexible shaft can particularly advantageously be used as a joint-free body or a joint-free extremity for a controllable endoscope. Owing to the connected wall sections of the shaft and the flexibility thereof, additional joining elements such as wiring pins, etc, having a relative movement against the body of the flexible shaft, are not necessary. It can, therefore, be advantageously created as a substantially maintenance-free component that can be inserted into an endoscope.

In a further embodiment, the flexible shaft could be formed as a rotating or rotatable driveshaft. Consequently, a unidirectionally movable driveshaft having a multi-axle freedom of movement is designed. Thus continually variable inflexion and bending are made possible. Furthermore, a rotational movement is conveyed between two axis transfer points. Consequently, an offset-compensating flexible drive shaft or coupling can be advantageously proposed.

Figure 2B:
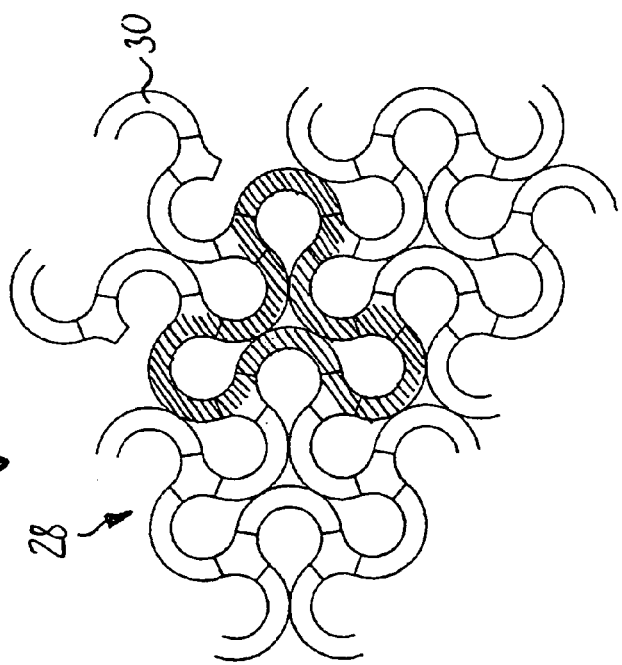
Figure 2A:
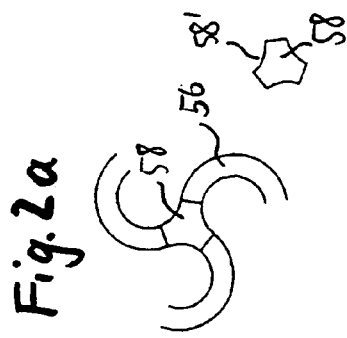
Figure 4:
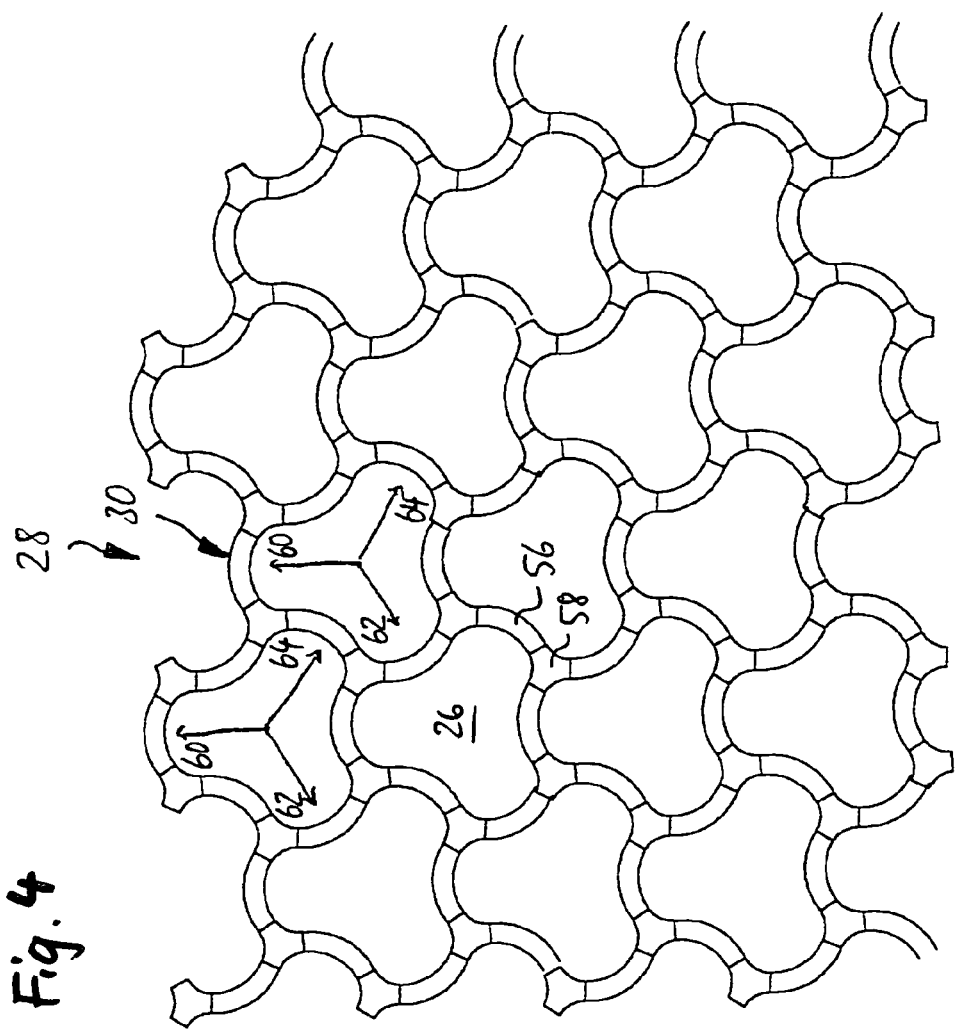
Figure 3:
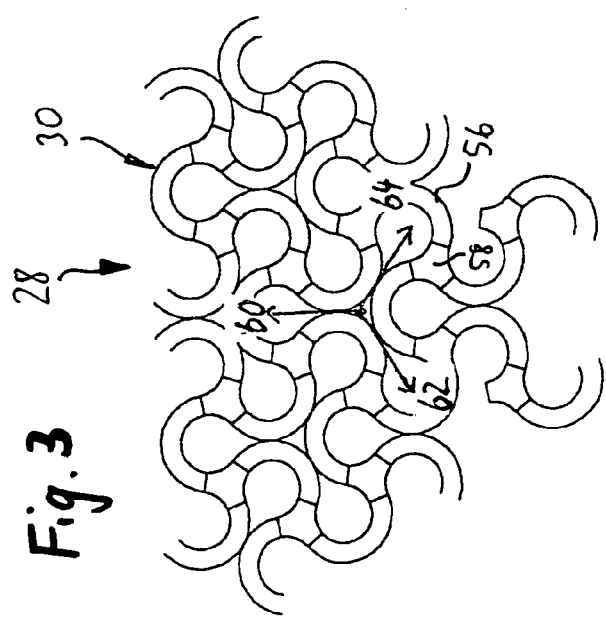
Figure 5:
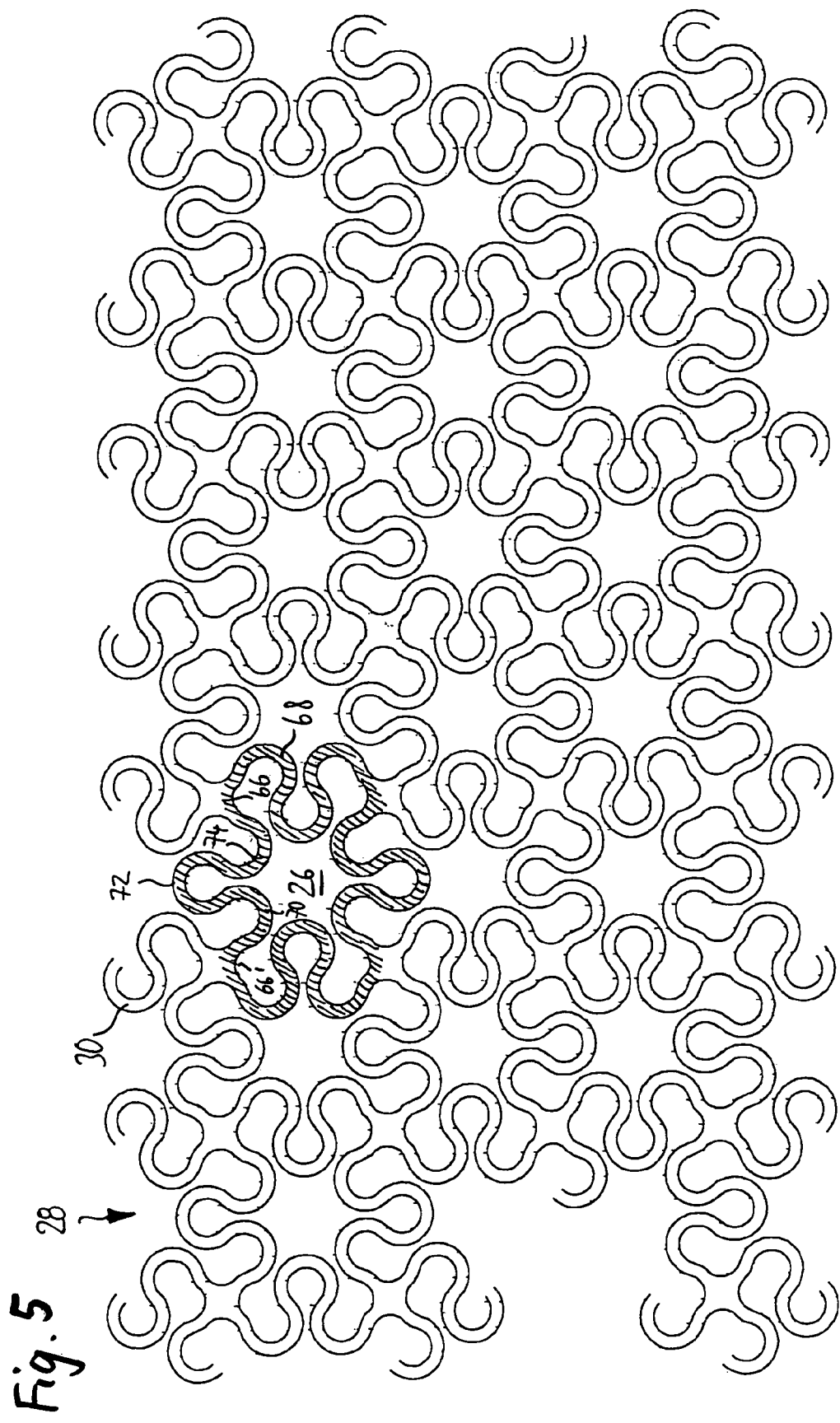
Figure 6:
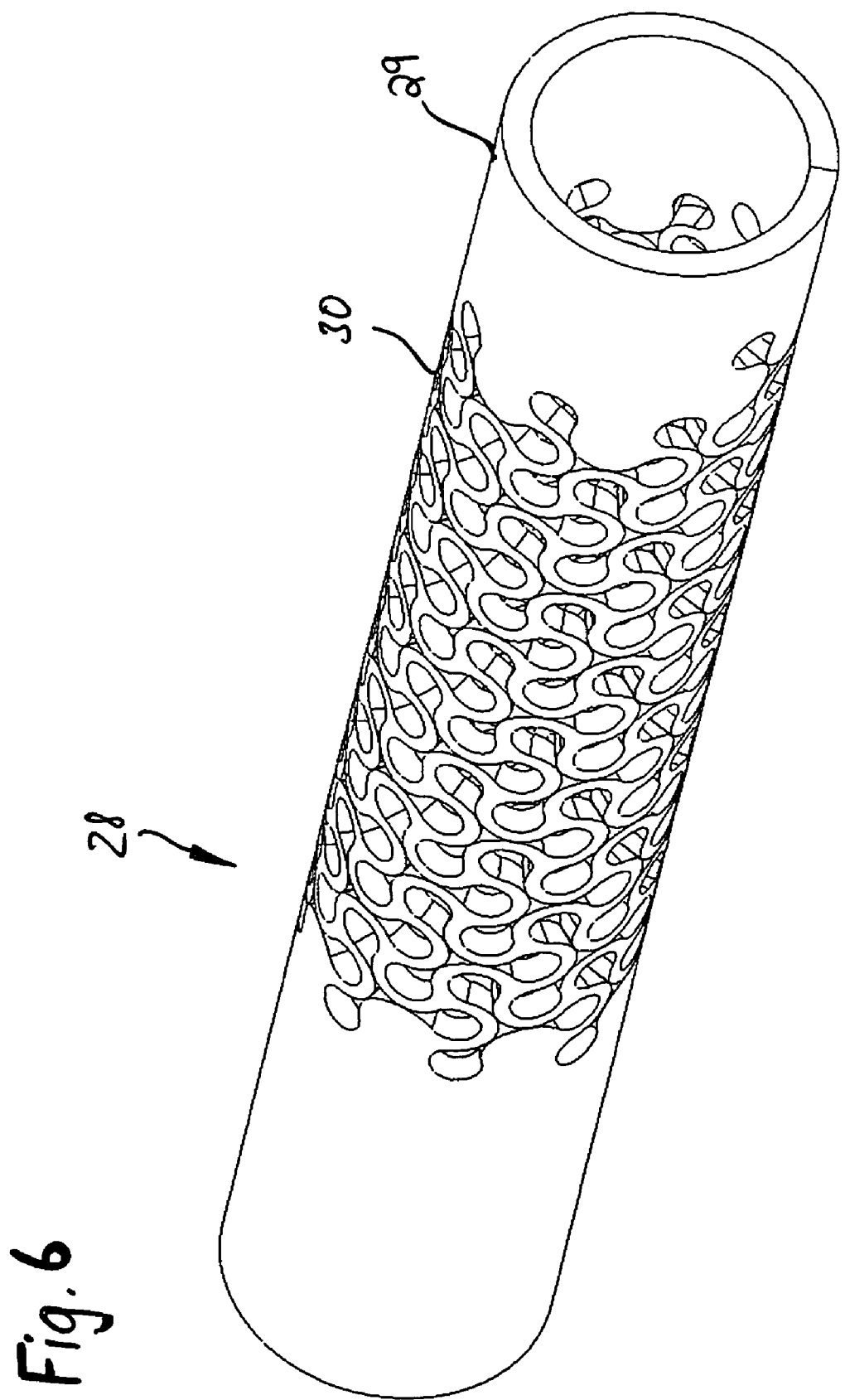

The embodiments of a shaft according to the invention with the accompanying schematic drawings are explained in more detail below:

FIGS. 1a to 1d A succession of diagrams showing the configuration of a cell of a first embodiment of a flexible shaft according to the invention;

FIGS. 2a to 2c A succession of diagrams showing the constitution of a structure of cells from a first embodiment of a flexible shaft according to the invention;

FIG. 3 A cross-section of the first embodiment of a flexible shaft according to the invention at a compressed structure section;

FIG. 4 A cross-section of the first embodiment of a flexible shaft according to the invention at a expanded structure section;

FIG. 5 A cross-section of the second embodiment of a flexible shaft according to the invention at a compressed structure section; and FIG. 6 A perspective view of the first embodiment of a flexible shaft according to the invention that is neither shaped or compressed.

According to a preferred embodiment of the invention, a flexible shaft and a plurality of at least spatially arranged cells 26, for at least one local bend or deformation of the flexible shaft, for adapting a body lumen or channel to a shape, for example, is known. In a curve or deformation of the flexible shaft, one or more of the cells 26 are expanded and/or compressed so that the resulting bend or deformation of the flexible shaft is possible.

The main configuration of a preferred cell 26 (see FIG. 1d) is disclosed in FIGS. 1a to 1d, said cell in combination with further cells forms a flexible area between two inflexible extremities of a flexible shaft 28 (see FIG. 6). The cell 26, has a wall 30 which is composed of individual wall sections.

FIG. 1a discloses a ring 32 that serves as a basic element for the individual wall sections.

Two further rings, 34 and 36, are theoretically attached to said ring 32. The walls of attached rings 34 and 36, rest on and overlap the corresponding wall of said first ring 32.

Three rings, 38, 40 and 42 are, in turn, theoretically attached to rings 34 and 36. The wall of ring 38 overlaps the wall of rings 34 and 40. The wall of ring 40 overlaps the wall of rings 38 and 42 and rests on the walls of rings 34 and 36. The wall of ring 42 overlaps the walls of rings 36 and 40.

Altogether, six rings are in this way connected into a triangle, whereby the walls of the rings in the outer part of the triangle, overlap each other and those in the central part of the triangle rest on each other (see FIG. 1b), respectively.

FIG. 1c discloses how the wall section of wall 30 of an individual cell 26 is constructed from the rings 32 to 42 positioned in this way.

In principle, when considered in cross-section, wall 30 is formed in a serpentine shape from concave and convex wall sections, respectively, said sections being circumferentially alternated around shaft 28. This will be explained in more detail below.

Three "corner areas" of shaft 28, composed of wall sections 44, 46 and 48 respectively, are disclosed according to the basic structure of the triangle in FIG. 1b. Wall sections 44, 46 and 48 are preferably circular and represent a part of rings 32, 38 and 42, respectively, as disclosed in FIG. 1b.

Wall sections 50, 52 and 54, derived from rings 34, 36 and 40, are located between concave wall sections 44, 46 and 48, respectively. Wall sections 50 and 52, 52 and 54 and 50 and 54, respectively, preferably rest on these wall sections when in the fully compressed state of a cell 30 as shown in FIG. 1c. In its compressed state, a cell 30 must imperatively not come into contact with wall sections 50, 52 and 54. It is also possible for a cell 30 to be only partially compressed and wall sections 50, 52 and 54 to be at least marginally cleared.

Thus the "folded" wall 30 of a cell 26 as shown in FIG. 1d is composed of concave and convex wall sections 44 to 54.

Flexible shaft 28 is composed of a substantially tubular member 29 having a plurality of adjacent cells 26 therein. Cell 26, shown in FIG. 1d is thus to be found again in a flexible shaft 28, such as that shown in FIG. 2b and FIG. 6.

As a result of combining cells 26, individual wall sections 44 to 54 of a cell 26, also together as a wall section to neighbouring cells, belong to a flexible shaft structure. This situation is shown in FIG. 2a to 2c.

The diagram in FIG. 2b shows that the walls 30 of a flexible shaft 28 can also be fundamentally considered to be the structured configuration of several rings 56 that are located between joints and joining elements 58. Thereby three arcs 56 stick out from a joint 58 respectively.

The individual arc 56 extends over an area of between 160° and 180°, over an angle of some 170° in particular. Its inner and outer edges, respectively, are constructed circularly in cross section so that its surface part represents a circular cylindrical flask. The wall of the individual arc 56 is preferentially of constant thickness. The individual joint 58 correspondingly joins three such arcs 56.

The joint 58 has three sides and extremities to which an arc 56 is connected. There is a concave curve 58' between the three extremities and the joint 58, said curve having a radius that substantially matches the inner radius of an arc 56. The curves of arc 56 also fit flush into the neighbouring curves 58' of the joint 58, in that they in turn close arc 56. The surface curve is constant at the point of transition.

The curves 58' of joints 58 and the inner surfaces of arc 56 form part of the concave wall areas 50, 52 and 54, described above. The convex wall sections 44, 46 or 48 are formed from the outer surfaces of arcs 56. The points of transition between arc 56 and joints 58 are thus markers of the existing curve, where a joint 58 borders on a convex wall section 44, 46 or 48 and also where a concave wall section passes over a neighbouring convex wall section.

FIGS. 3 and 4 show how a flexible shaft 28 in its compressed and unshaped condition as shown in FIG. 2c is turned into a partially expanded and curved structure. The three individual parts of wall 30 are deployed at the curves of the shaft and its sectional cell expansions, said parts being formed in three outward directions 60, 62 and 64, from corresponding convex and neighbouring concave wall sections. There is an angle of 120° respectively, between each of the directions.

As shown by FIG. 4, in particular, a cell area of the thus formed flexible shaft is equally expanded in directions 60, 62 and 64, whereby the above, in combination with the invention displays the above-mentioned advantages.

A second embodiment of a flexible shaft 28 is shown in FIG. 5, in which a plurality of wall areas 68 are formed between the joints or joining elements 66. The plurality of wall areas 68 formed are one of three units created in the form of substantially half-circular arcs 70, 72 and 74, which are constructed back-to-back, convex, concave and a further convex wall section, with the annotated cell 26. These arcs are built together with a concave, a convex and a further concave wall section in a neighbouring cell.

The individual arcs 70, 72 and 74 cover an angle of some 150° to 250°, preferably approximately 200°. Their surface corresponds substantially to a section of a circular cylinder. The thickness of the wall of the arcs 70, 72 and 74 is substantially constant.

The joints 66 have four sides or extremities, each one being connected to a wall section 68. Curves 66' are located between these extremities, said curves having a radius that corresponds to the inner radius of one of arcs 70, 72 or 74. A single joint 66 is thus formed so that, when considered in cross-section, it is substantially circular. The point of transition between a joint 66 and an arc 70, 72 or 74 is fluent and flush and formed without flange. The curve of the surface at the point of transition is, in turn, substantially constant. The individual concave arcs 66' on joints 66 cover an angle of approximately 70° to 110°, preferably being some 90°.

The wall 30 of a cell 26 of the flexible shaft 28, also shown in the embodiment of FIG. 5, is thus completely formed from alternated concave and convex wall sections, which, when considered in cross-section each have the basic form of an arc or a ring, respectively. Four such wall areas 68 are connected to a joint 66. The structure of the flexible shaft according to that shown in FIG. 5 leads to a preferred simultaneous expansion in 4 directions. Flexible "spider-shaped" shafts are, however, conceivable in that cells are at least partially arranged, which are completely formed from alternated concave and convex wall sections and to the joints of which five or more wall areas are connected.

The flexible shaft according to the invention or a preferred embodiment thereof can just as well be made from rough as from flat material, whereby the latter flexible shaft is to be rolled, welded and finished later. In addition, the flexible shaft can be made from laser cut, laser removed, photochemically etched and/or eroded substances. Furthermore, the flexible shaft can also be made following the method by which the flexible shaft structure is prepared in an at least partially expanded form and that the flexible shaft adjacent to a compressed form will be reduced before it is subsequently shaped on insertion into a body and thereby again at least partially expanded.

According to a preferred embodiment of the invention the flexible shaft will be used for disposition or insertion of an expanding structure in a hollow organ, which extends from a first connection section substantially lengthwise to a second connection section, over the circumference the expanding structure is orderly distributed and, through radial branches can be attached to the wall of a hollow organ.

The type of expanding structure mentioned above can be inserted, with the help of the flexible shaft, as a temporary or long-term implant in a hollow organ such as, for example, the heart, the arteries, the biliary tract, the urinary tract, the gastrointestinal tract, the uterus and the himventrikel so as to retard thrombosis or gallstones, for example.

Different types of thrombosis filters using a percutaneous vein implant in the vena femoralis or the vena jugularis in the upper or lower vena cava are known. Said implants should stop the thrombosis on its way to the heart and thereby prevent a pulmonary embolism. Such implants are, in general, formed with conical extremities or rods, formed from a tri-form filter cage. Furthermore, the flexible shaft can be used to dispose a metal electrode, in order to warm up one wall of the hollow organ and thus, for example, carry out electrocoagulation.

Again, the flexible shaft can be used advantageously to dispose or insert endoprostheses (preferably self-expansible) into vein-like structures to keep them open, such as the so-called stents that can also be inserted into arteries. Stents are, in general, formed from a hose-like, more or less finely woven wire cloth or netting, which is expansible under an elastic restoring force.

The flexible shaft is advantageously designed to be substantially reforming for such applications and an equally expansible shaft, rod or tube can be placed therein, by means of which the expansible structure or metal electrode or stent can be manipulated (i.e. expanded and/or contracted and outer circumference reduced), by means of the relative adjustment or displacement of the expansible shaft in relation to the tubular shaft.

What is claimed is:

1. A flexible shaft for inserting and disposing products for medical treatment into a channel of a living body, the shaft comprising:
    a substantially tubular member having a central axis; and
    a plurality of abutting cells forming at least part of the tubular member, at least one of the cells defined by a peripheral wall, each cell having at least three concave sections and at least three convex sections;
    wherein the concave sections alternate circumferentially with the neighboring convex sections and wherein the concave sections and convex sections are arranged to be approximately radially symmetrical about a center point of the cell;
    wherein each concave section and each convex section is in the form of a cylindrical arc having a consistent radius and wherein the cylindrical arc having a consistent radius extends over an area between 150 to 250 degrees;
    wherein upon radial expansion of the tubular member about the central axis, the convex sections of the cell extend radially outward from the center point of the cell, and further
    wherein the tubular member is expandable within the channel of the living body; and
    wherein the flexible shaft is configured to have a torsion rigidity, which allows the insertion into small and constricted serpentine vessels.

2. The flexible shaft of claim 1, wherein the flexible shaft is a flexible intraluminal shaft.

3. The flexible shaft of claim 1, wherein at least one convex section is formed with a curved radius that is substantially equal to the curved radius of a neighboring wall.

4. The flexible shaft of claim 3, wherein the convex and concave sections are substantially identical.

5. The flexible shaft of claim 4, further comprising a compressed cell defined by a peripheral wall, a cross-section of which has at least three convex sections, wherein the convex sections have at least one adjacently abutting cell.

6. The flexible shaft of claim 5, wherein the flexible shaft has a lubricating surface coating.

7. The flexible shaft of claim 6, wherein the flexible shaft is expandable to create an opening for inserting at least one of an expandable structure, a metal electrode and an endoprostheses in at least one of a hollow organ and a lumen.

8. The flexible shaft of claim 1, wherein the flexible shaft forms a highly flexible tip or a highly flexible distal extremity for a guide-wire.

9. The flexible shaft of claim 1, wherein the cells form a flexible area between two inflexible extremities of the flexible shaft.

10. In a flexible shaft for inserting and disposing products for medical treatment into a channel of a living body, the flexible shaft having a substantially tubular member with a central axis and a plurality of abutting cells each defined by a peripheral wall, the improvement comprising:
    a cross-section of the cell having at least three concave sections and at least three convex sections wherein the concave sections and convex sections are arranged to be approximately radially symmetrical about a center point of the cell, wherein upon radial expansion of the tubular member about the central axis, the convex sections of the cell extend radially outward from a the center point of the cell, and further wherein the tubular member is expandable within the channel of the living body;
    wherein each concave section and each convex section is in the form of a cylindrical arc having a consistent radius and wherein the cylindrical arc having a consistent radius extends over an area between 160 and 180 degrees;
    wherein the flexible shaft is configured to have a torsion rigidity, which allows the insertion into small and constricted serpentine vessels.

11. The flexible shaft of claim 10, wherein at least one cell has the concave section circumferentially alternating with a neighboring convex section.

12. The flexible shaft of claim 10, wherein at least one convex section is formed with a curved radius that is substantially equal to the curved radius of a neighboring wall.

13. The flexible shaft of claim 10, wherein the convex and concave sections are substantially identical.

14. The flexible shaft of claim 10, further comprising a compressed cell defined by a peripheral wall, a cross-section of which has at least three convex sections, wherein the convex sections have at least one adjacently abutting cell.

15. The flexible shaft of claim 10, wherein the flexible shaft has a lubricating surface coating.

16. The flexible shaft of claim 10, wherein the flexible shaft is expandable to create an opening for inserting at least one of an expansible structure, a metal electrode and an endoprostheses in at least one of a hollow organ and a lumen.

17. The method of manufacturing a flexible shaft for insertable inserting and disposing products for medical treatment into a channel of a living body, the method comprising:
- providing a substantially tubular member having a central axis;
- forming a plurality of abutting cells in the tubular member, at least one of the cells defined by a peripheral wall, a cross-section of the cell having at least three concave sections and at least three convex sections,
- wherein the cell is defined by the peripheral wall having the concave sections circumferentially alternating with a neighboring convex sections and wherein the concave sections and convex sections are arranged to be approximately radially symmetrical about a center point of the cell,
- wherein each concave section and each convex section is in the form of a cylindrical arc having a consistent radius and wherein the cylindrical arc having a consistent radius extends over an area between 160 and 180 degrees;
- wherein upon radial expansion of the tubular member about the central axis, the convex sections of the cell extend radially outward from a center point of the cell, and further
- wherein the tubular member is expandable within the channel of the living body
- wherein the flexible shaft is configured to have a torsion rigidity, which allows the insertion into small and constricted serpentine vessels.

18. The method of claim 17 wherein at least one concave section of the at least three concave sections abuts at least two of the at least three concave sections along the peripheral wall.

* * * * *